(12) United States Patent
Fukui

(10) Patent No.: US 7,459,714 B2
(45) Date of Patent: Dec. 2, 2008

(54) IMAGE RECORDING CARRIER

(75) Inventor: Shinichiro Fukui, Kanagawa (JP)

(73) Assignee: Fujifilm Corporation, Minato-ku (JP)

( * ) Notice: Subject to any disclaimer, the term of this patent is extended or adjusted under 35 U.S.C. 154(b) by 0 days.

(21) Appl. No.: 11/812,644

(22) Filed: Jun. 20, 2007

(65) Prior Publication Data

US 2007/0297573 A1    Dec. 27, 2007

(30) Foreign Application Priority Data

Jun. 23, 2006   (JP)   ............... 2006-173780

(51) Int. Cl.
  *G01N 23/02*   (2006.01)
(52) U.S. Cl. ............... 250/581; 250/582; 250/583; 378/37
(58) Field of Classification Search ............... 378/37
See application file for complete search history.

(56) References Cited

U.S. PATENT DOCUMENTS

| | | | | |
|---|---|---|---|---|
| 4,851,690 A | * | 7/1989 | Teraoka | ............... 250/484.4 |
| 5,340,661 A | * | 8/1994 | Van Havenbergh et al. | . 428/690 |
| 5,441,251 A | * | 8/1995 | Ohta | ............... 271/145 |
| 2005/0155886 A1 | * | 7/2005 | Nakajo | ............... 206/455 |
| 2006/0065852 A1 | | 3/2006 | Fukui et al. | |

FOREIGN PATENT DOCUMENTS

| | | |
|---|---|---|
| JP | 2003-248093 A | 9/2003 |
| JP | 2006-105597 A | 4/2006 |

* cited by examiner

*Primary Examiner*—David P. Porta
*Assistant Examiner*—Yara B Green
(74) *Attorney, Agent, or Firm*—Birch, Stewart, Kolasch & Birch, LLP

(57) ABSTRACT

An image recording carrier includes: an image recording plate including a plate-shaped supporter, and a recording layer which is superposed on the top of the supporter, and which accumulates and recodes a radiograph when irradiated with radioactive rays carrying an image; and a cassette in which the image recording plate is housed. Multiple steps are formed in the direction along the thickness of the image recording plate on at least one side surface of the image recording plate, and a front portion which is one of the multiple steps including the recording layer, protrudes from the rest of the multiple steps. A facing surface of the cassette facing the side surface of the image recording plate while the image recording plate is housed in the cassette has an opposed portion which is opposed to the front portion, and which dents from the rest of the multiple steps.

9 Claims, 5 Drawing Sheets

IMAGE RECORDING CARRIER

BACKGROUND OF THE INVENTION

1. Field of the Invention

The present invention relates to an image recording carrier which accumulates and records a radiograph when irradiated with radioactive rays carrying an image to be radiographed.

2. Description of the Prior Art

Heretofore, there have been known radioactive-energy-accumulating fluorescent substances which accumulate part of radioactive energy when irradiated with radioactive rays, and which emit photostimulated luminescent light depending on the accumulated radioactive energy when irradiated with a beam of visible light or the like. Recent years, CR (computed radiography) has been in increasingly wide use in the medical field and the like. CR is a technique as follows. A radiograph is accumulated and recorded in a radioactive-energy-accumulating fluorescent substance by irradiating the radioactive-energy-accumulating fluorescent substance with radioactive rays having passed through an object. Subsequently, the radioactive-energy-accumulating fluorescent substance is irradiated with excitation light, and thus photostimulated luminescent light is emitted from the radioactive-energy-accumulating fluorescent substance. By reading the photostimulated luminescent light thus emitted, the radiograph is visualized.

There are two types of image reading apparatuses which are widely used for medical CR: a built-in type and a cassette type. In the case of image reading apparatuses of the built-in type, an IP (imaging plate) and a reading section are altogether housed in a single apparatus body, and thus the IP housed in the single apparatus is irradiated with radioactive rays. The IP is obtained by adhering a radioactive-energy-accumulating fluorescent substance to a surface of a substrate. The reading section irradiates the IP with a laser beam or the like, and thus reads the resultant photostimulated luminescent light. Image reading apparatuses of the built-in type will be hereinafter referred to as "built-in apparatuses." In the case of image reading apparatuses of the cassette type, an IP is housed in a portable cassette. A radiograph is accumulated on the IP through radiographing. This IP is housed in the cassette. This cassette is attached to an image reading apparatus. The image reading apparatus takes the IP out of the cassette, and thus reads the radiograph. Image reading apparatuses of the cassette type will be hereinafter referred to as "cassette apparatuses."

Built-in apparatuses make it possible to read a radiograph made on the spot, and thus to check on the radiograph immediately. This makes it possible for a user to find a failure in radiographing immediately, and to take another shot. For this reason, built-in apparatuses are widely used for a group physical checkup, which requires radiographs to be taken of multiple objects securely.

On the other hand, in the case of cassette apparatuses, a cassette can be easily moved closer to a part of an object which is intended to be radiographed during radiographing. In a case where, for example, a patient has his/her bone fractured, a cassette apparatus is capable of radiographing an injured part which is intended to be radiographed without forcing the patient to get into uncomfortable poses. In addition, in a case where, for example, an IP is damaged in a cassette, the damaged IP housed in the cassette can be easily replaced with a spare IP. This brings about an advantage that time and costs needed to resume radiographing can be saved to a large extent.

As described above, since the built-in apparatuses and the cassette apparatuses have different advantages, many hospitals are furnished with both a built-in apparatus and a cassette apparatus in many cases. Usually, they use one of the two types of apparatuses depending on an intended use.

Moreover, in recent years, mammography apparatuses have become in use. The mammography apparatuses radiograph a mamma while flattening the mamma with the mamma placed and pressed between an IP and a transmission plate having a radioactive transmittivity. The mammography apparatuses are known for their effectiveness for early detection of breast cancer. In many cases, whether or not hospitals are furnished with a mammography apparatus is an important criterion for patients to choose their hospitals.

There are also two types of mammography apparatuses: a built-in type and a cassette type. In the case of mammography apparatuses of the built-in type, an IP and a reading section in addition to a pressing mechanism and an irradiation unit are altogether housed in a single mammography apparatus body. The reading section reads a radiograph. The pressing mechanism presses a transmission plate toward the IP. The irradiation unit irradiates the IP with radioactive rays. In the case of mammography apparatuses of the cassette type, only elements such as a pressing mechanism and an irradiation unit are installed in a single mammography apparatus body. A cassette in which an IP is housed is attached to the mammography apparatus, and is irradiated with radioactive rays. When using a mammography apparatus of this cassette type, a mamma is radiographed by placing the mamma between the attached cassette and a transmission plate. The cassette which has been used for the radiographing is attached to an image reading apparatus which is equipped separately from the mammography apparatus. Thus, a radiograph which has been accumulated and recorded on the IP is read by the image reading apparatus. In the case of mammography apparatuses of this cassette type, it is easy to replace a damaged IP with a new one. In addition, the conventional cassette apparatuses which have been used in hospitals can be used as image reading apparatuses for reading a radiograph. For these reasons, the mammography apparatuses of the cassette type are more cost-effective and more easy to be introduced than mammography apparatuses of the built-in type.

In a case where a mamma is going to be radiographed by use of a mammography apparatus of the cassette type, a side surface of a cassette is pressed against the base of the mamma (the base of the mamma will be referred to as a "chest wall"), and the mamma is irradiated with radioactive rays while the mamma being flattened on the top surface of the cassette by use of a transmission plate. At this time, the mammography apparatus is incapable of accumulating or recording the radiograph corresponding to a part of the IP housed in the cassette even though the IP is irradiated with the radioactive rays. The part in question extends from a place corresponding to the side surface of the cassette to a place beyond which a radioactive-energy-accumulating fluorescent substance is adhered to the IP. This part in question will be hereinafter referred to as an "unrecorded part." Because of an unrecorded part of this kind, mammography apparatuses of the cassette type have a problem that a part of a mamma which is closer to the chest wall is missing from a radiograph of the mamma.

With regard to this problem, Japanese Patent Application Laid-open Publication No. 2003-248093 (hereinafter referred to as "JPA-2003-248093") has disclosed a technique with which an IP is produced by expanding a recording area for accumulating and recording a radiograph in an IP up to the end of a substrate. More specifically, a layer of a radioactive-energy-accumulating fluorescent substance is formed in a place between 0.0 mm and 0.4 mm from the end of the substrate. The technique disclosed by JPA-2003-248093 makes it possible to reduce the unrecorded part in the area, and to accordingly decrease a missing portion of a radiograph.

It is usual, however, that a cassette is configured of a plastic or the like with a thickness of approximately several millimeters. Even though a recording area of an IP is intended to be expanded by use of the technique disclosed by JPA-2003-248093, in reality, a portion of a mamma in a range of the chest wall to approximately 5 mm therefrom is incapable of being radiographed because of the thickness of a plastic of which the cassette is configured. This means that mammography apparatuses of the cassette type are incapable of radiographing a tumor closer to the chest wall until the tumor develops beyond a range of the chest wall to approximately 5 mm therefrom. This incapability places an obstruction to breast cancer checks which aim at earlier detection of breast cancers. On the other hand, if an unrecorded part is intended to be reduced in area by forming a cassette of a thinner plastic, this decreases the strength of the cassette. This brings about a problem that a hard but fragile IP can not be protected by the cassette securely.

SUMMARY OF THE INVENTION

The present invention has been made in view of the above circumstances, and provides an image recording carrier which is capable of reducing a missing portion from a radiograph made by a radiography apparatus such as a mammography apparatus without decreasing the strength of the cassette.

An image recording carrier according to the present invention includes:

an image recording plate including a plate shaped supporter and a recording layer which is superposed on a top surface of the supporter, and which accumulates and records a radiograph when irradiated with radioactive rays carrying an image; and a cassette in which the image recording plate is housed, wherein the image recording plate has multiple steps formed in a direction along a thickness of the image recording plate on at least one side surface of the image recording plate, and has a front portion which is one of the multiple steps including the recording layer and which protrudes from the rest of the multiple steps, the cassette has a facing surface facing the side surface of the image recording plate while the image recording plate is housed in the cassette, and an opposed portion of the facing surface being opposed to the front portion of the image recording plate dents from the rest of the multiple steps.

In the image recording carrier according to the present invention, the front portion including the recording layer in which the radiograph is accumulated and recorded protrudes above the rest of the side surface of the image recording plate. The opposed portion in the facing surface of the cassette, which id opposed to the front portion, dents under the rest of the facing surface. Once the image recording plate is housed in the cassette, the front portion of the image recording plate is fitted into the opposed portion of the cassette, and thus comes closer to the side surface of the cassette. This makes it possible to reduce a missing portion of a radiograph which is made of the mamma when pressing the side surface of the cassette against the chest wall of an object. In addition, the protruding of the facing surface of cassette except for the opposed portion makes it possible to increase the strength of the cassette while causing the recording layer of the image recording plate to remain closer to the side surface of the cassette without increasing the missing portion of the radiograph.

In the image recording carrier according to the present invention, it is desirable that the front portion of the image recording plate should be beveled.

The beveling, such as the chamfering, of the front portion of the image recording plate makes it possible to suppress a disadvantage that the recording layer is damaged due to a shock which may occur while the image recording plate is being housed in the cassette.

In the image recording carrier according to the present invention, it is desirable that the opposed portion of the cassette should be beveled.

The processing of the opposed portion of the cassette with an angle R makes it possible to avoid a disadvantage that the front portion of the image recording plate hits the opposed portion of the cassette so that the front portion is chipped off.

In the image recording carrier according to the present invention, it is desirable that the cassette should include a press member which presses the image recording plate housed in the cassette toward the facing surface.

Pressing the image recording plate toward the facing surface makes it possible to decrease a space between the front portion of the image recording plate and the opposed portion of the cassette, and to thus reduce the missing portion of the radiograph securely.

In the image recording carrier according to the present invention, it is desirable that the opposed portion of the cassette should be configured of a material which changes in shape when a force is applied to the material so that the opposed portion dents when the press member presses the front portion against the opposed portion.

Because the opposed portion of the cassette dents when the front portion of the image recording plate is pressed against the opposed portion, this dent makes it possible to securely avoid the image recording plate being damaged even when there occurs a dimensional error such as a too large amount of protrusion of the front portion of the image recording plate.

In the image recording carrier according to the present invention, it is desirable that an amount of dent of the opposed portion of the cassette should be larger than an amount of protrusion of the front portion.

Because an amount of dent of the opposed portion of the cassette is larger than an amount of protrusion of the front portion of the image recording plate, this enlargement makes it possible to prevent the front portion of the image recording plate from hitting the opposed portion of the cassette, and to thus suppress damage on the recording layer, while the image recording plate is being housed in the cassette.

In the image recording carrier according to the present invention, it is desirable that the opposed portion of the cassette should include a shock absorbing member which absorbs a shock which occurs when the front portion hits the opposed portion.

The image recording carrier according to the present invention makes it possible to efficiently reduce damage on the recording layer of the image recording plate.

In the image recording carrier according to the present invention, it is desirable that an edge of the recording layer of the image recording plate should be provided with a protection member which protects the edge.

Presence of the protection member on the edge of the recording layer makes it possible to reduce damage on the recording layer, and to concurrently protect the recording layer from deterioration which occurs due to higher humidity.

It is desirable that the image recording carrier according to the present invention should be attached to a mammography apparatus.

Because the mammography apparatus has a problem that there is a missing portion of a radiograph which is closer to the chest wall, it is desirable that the image recording carrier according to the present invention should be capable of being applied to the mammography apparatus.

The present invention makes it possible to reduce a missing portion from a radiograph made by a radiography apparatus such as a mammography apparatus without decreasing the strength of the cassette.

DETAILED DESCRIPTION OF THE INVENTION

Figure 1:
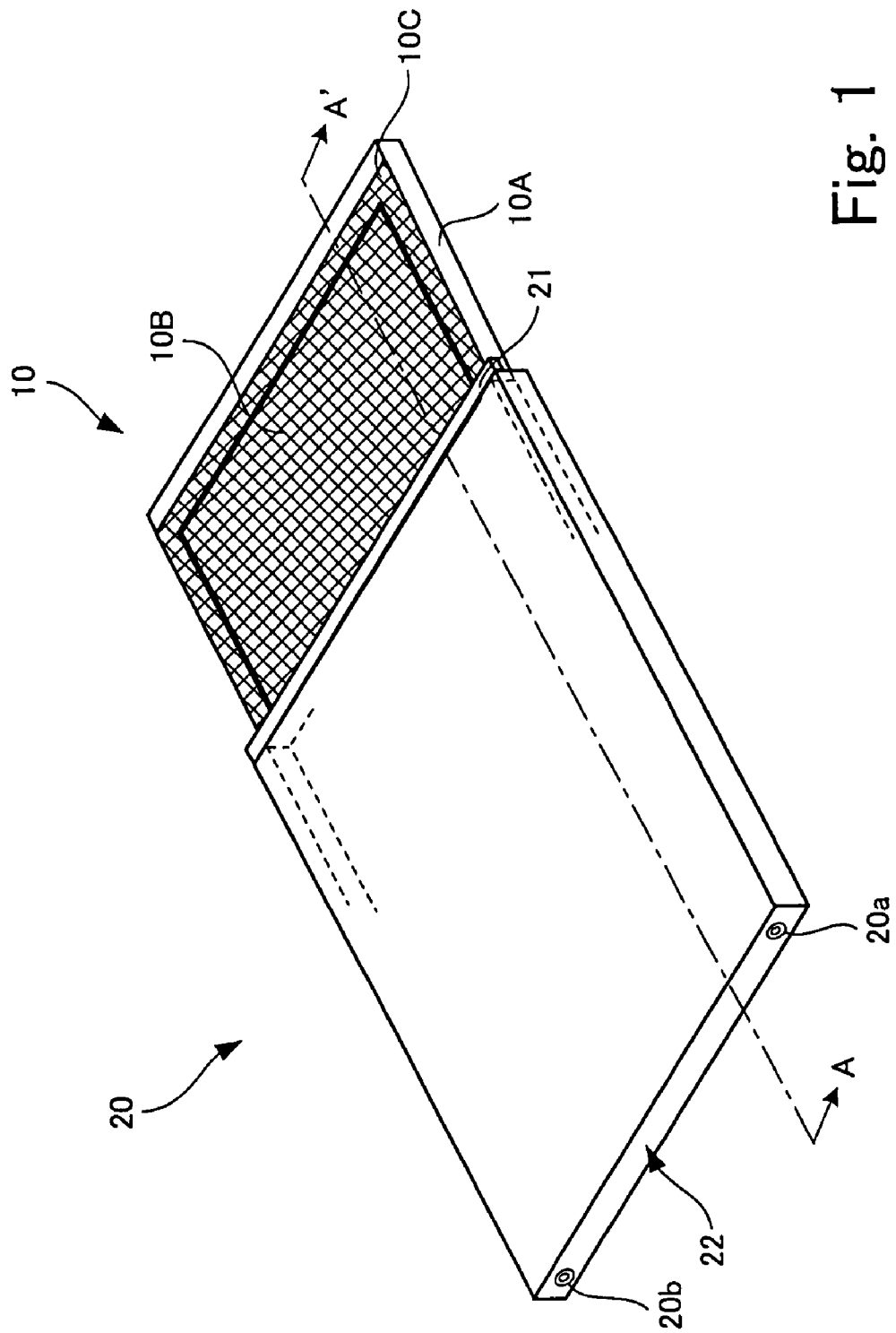
FIG. 1 is a diagram of a schematic configuration of an IP and a cassette according to a first embodiment of the present invention.

Descriptions will be provided hereinafter for embodiments of the present invention by referring to the drawings.

In the embodiments, a radiograph is accumulated and recorded in an IP. This IP is housed in a portable cassette. The cassette is attached to a mammography apparatus, and thus the radiograph is made. After radiographing, the cassette is attached to an image reading apparatus, and thereby the image reading apparatus reads the radiograph. First of all, descriptions will be provided below for a schematic configuration of the IP and the cassette.

FIG. 1 is a diagram of a schematic configuration of an IP and a cassette according to a first embodiment of the present invention.

As shown in FIG. 1, an IP 10 is housed in a cassette 20 in the present embodiment. The IP 10 is irradiated with radioactive rays, and thus a radiograph is accumulated and recorded on the IP 10. The cassette 20 is formed of a plastic allowing the radioactive rays to pass therethrough. The IP 10 is an example of the image recording plate as recited in the present invention. The cassette 20 is an example of the cassette as recited in the present invention. In addition, a combination of the IP 10 and the cassette 20 represents the image recording carrier as recited in the first embodiment of the present invention.

The IP 10 is formed by adhering a sheet 10B of a radioactive-energy-accumulating fluorescent substance to a substrate 10A. The edges of the sheet 10B of the radioactive-energy-accumulating fluorescent substance are provided with a resin-made protection material 10C so as to prevent the sheet 10B of the radioactive-energy-accumulating fluorescent substance from being chipped off or damaged in the like manner. The substrate 10A is an example of the supporter as recited in the present invention. The sheet 10B of the radioactive-energy-accumulating fluorescent substance is an example of the recording layer as recited in the present invention. The protection material 10C is an example of the protection material as recited in the present invention.

In addition, a side surface of the cassette 20 is provided with a lid 21. A side surface 22 of the cassette 20 on a side opposite to the side surface provided with the lid 21 is provided with push holes 20a and 20b which are configured to push the IP out of the cassette 20 when a pin is inserted in each of the push holes 20a and 20b. When the IP 10 is taken out of the cassette 20, the lid 21 is opened. Subsequently, a pin is inserted in each of the push holes 20a and 20b, and thereby the IP 10 is discharged out of the cassette 20. It should be noted that, in a case where this cassette 20 is attached to a mammography apparatus (described later) configured to radiograph a mamma of an object, the cassette 20 is attached thereto in such a way that the side surface 22 of the cassette 20 on the side opposite to the side surface provided with the lid 21 faces the object. Subsequently, the side surface 22 is brought into contact with the chest wall of the object. The side surface 22 will be hereinafter referred to as a "contact side surface 22."

Thereafter, descriptions will be provided below for a radiograph, which is accumulated and recorded on the IP 10 housed in the cassette 20 as shown in FIG. 1.

Figure 2:
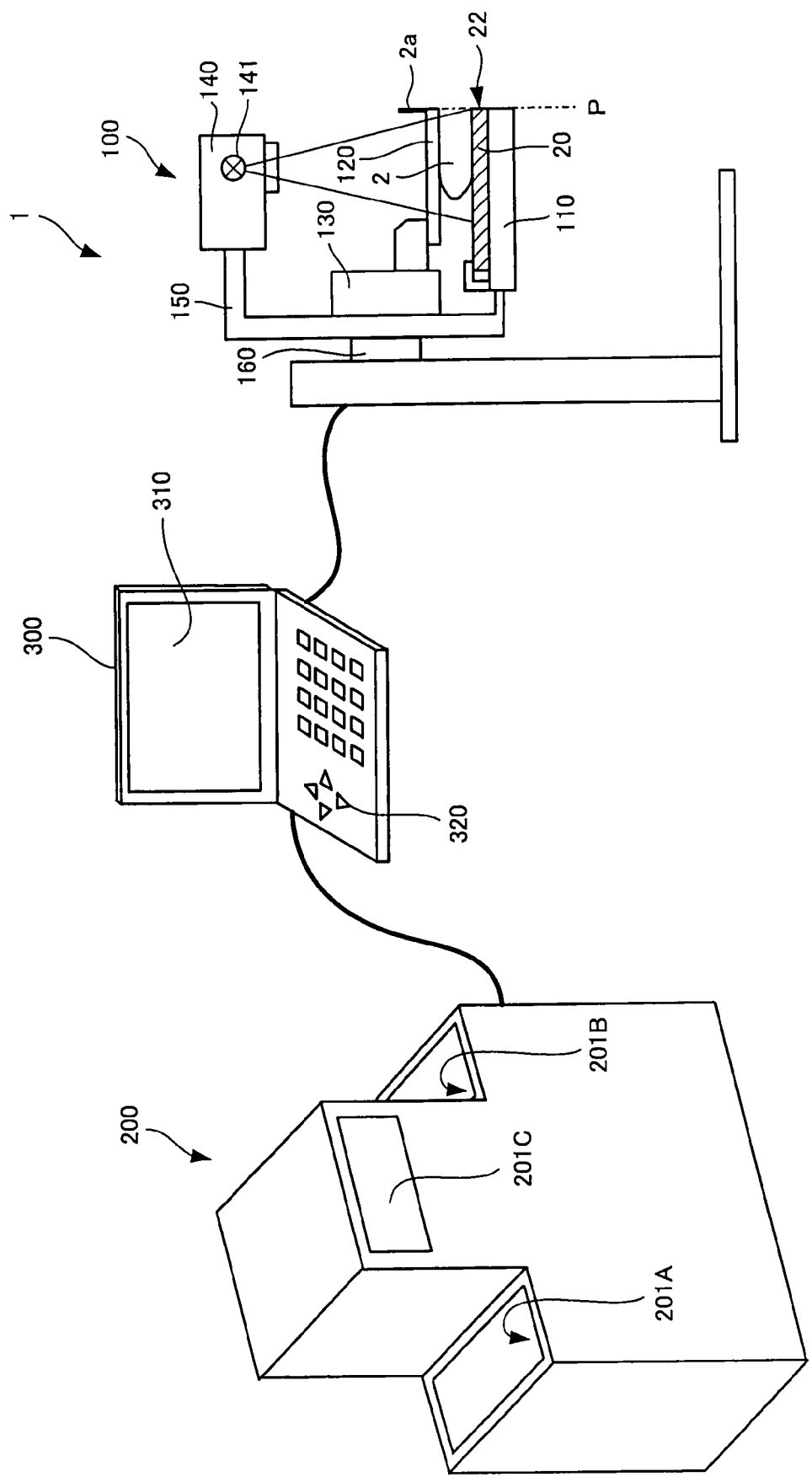
FIG. 2 is a diagram showing a schematic configuration of a radiography system.

FIG. 2 is a diagram showing a schematic configuration of a radiography system.

A radiography system 1 as shown in FIG. 2 comprises a mammography apparatus 100, an image reading apparatus 200 and a controller 300. The mammography apparatus 100 radiographs a mamma of an object. The image reading apparatus 200 reads the radiograph which is accumulated and recorded on the IP 10. The controller 300 displays the radiograph which has been read by the image reading apparatus 200, and controls the entire radiography system 1.

The controller 300 includes a display monitor 310 and operation buttons 320 when viewed from the outside. The display monitor 310 displays the radiograph read by the image reading apparatus 200. The operation buttons 320 are used by a user for input instructions.

The mammography apparatus 100 includes an attachment base 110 to which the cassette 20 housing the IP 10 is to be attached, a transmission plate 120 through which radioactive rays are to pass, a plate driving section 130 which moves the transmission plate 120 in the upward and downward directions, a radioactive ray irradiating section 140, a supporter 150 and a supporter driving section 160 when viewed from the outside. The radioactive ray irradiating section 140 is provided with a tube 141 configured to emit radioactive rays. The supporter 150 supports the attachment base 110 and the radioactive ray irradiating section 140. The supporter driving section 160 moves the supporter 150 in the upward and downward directions. A controlling section (not illustrated) is installed in the mammography apparatus 100. The controlling section controls the entire mammography apparatus 100 in accordance with instructions transmitted from the controller 300.

When taking a radiograph, first of all, the contact side surface 22 of the cassette 20 is aligned with a predetermined radiographing position P, and thus attached to the top of the attachment base 110.

Once the cassette 20 is attached to the attachment base 110, an object is moved to the front of the mammography apparatus 100. A user adjusts the position of the attachment base 110 to the position of a mamma 2 of the object by use of operation buttons 320. Thereby, a chest wall 2a of the object is pressed to the contact side surface 22 of the cassette 20 located at the radiographing position P.

Subsequently, the user inputs an instruction for radiography preparation by use of the operation buttons 320 of the controller 300. The instruction for the radiography preparation is transmitted to the mammography apparatus 100. Thereby, the plate driving section 130 moves the transmission plate 120 in the downward direction. Thus, the mamma 2 of the object is placed between the transmission plate 120 and the cassette 20, and the mamma 2 is flattened. Thereafter, the radioactive ray irradiating section 140 irradiates radioactive rays on the mamma 2.

The radioactive rays emitted from the radioactive ray irradiating section 140 passes through the mamma 2, and further passes into the cassette 20. Thus, the IP 10 housed in the cassette 20 is irradiated with the radioactive rays. As a result, a radiograph of the mamma 2 is accumulated and recorded on the IP 10.

Once the radiographing is completed, the IP 10 as housed in the cassette 20 is removed from the cassette 20 to be attached to the image reading apparatus 200.

Both ends of the image reading apparatus 200 are each provided with a loading port 201A in which the cassette 20 is to be loaded and a discharging port 201B from which the cassette 20 is configured to be discharged once the image reading apparatus 200 completes reading the radiograph. The center of the image reading apparatus 200 is provided with a display panel 201C on which an operational status and the like of the image reading apparatus 200 is to be displayed. The cassette 20 which has been used for the radiographing is to be inserted in the loading port 201A.

Figure 3:
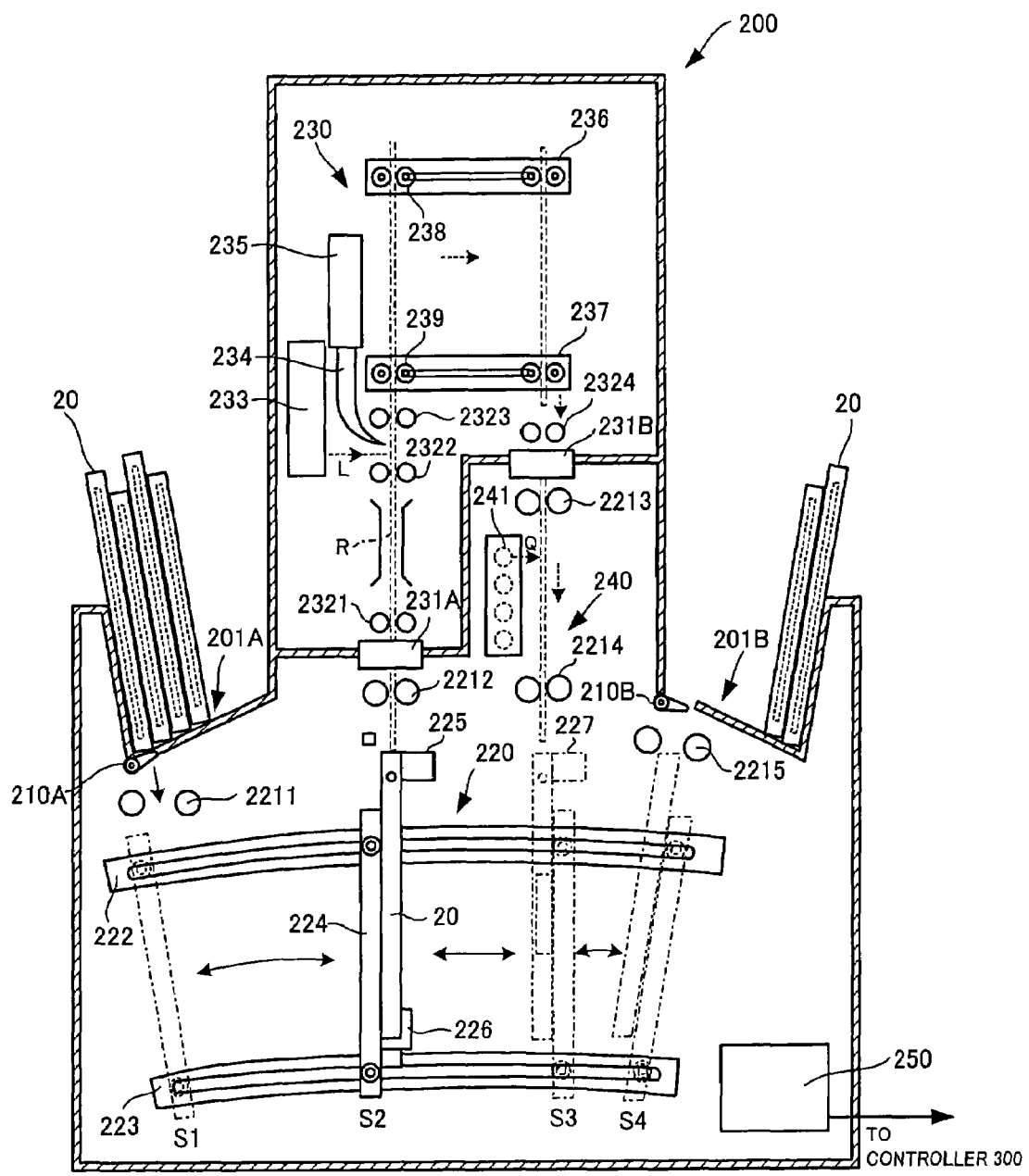
FIG. 3 is a diagram showing an inner configuration of an image reading apparatus.

FIG. 3 showing a diagram showing an inner configuration of the image reading apparatus 200.

As shown in FIG. 3, the bottom of the loading port 201A declines such that a portion thereof becomes lower as it is located farther away from the center of the image reading apparatus 200. The lowermost portion of the decline is provided with a lid member 210A through which the cassette 20 is to be taken into the interior of the image reading apparatus 200. In addition, the loading port 201A is provided with a sensor (not illustrated) configured to detect whether or not the cassette is attached thereto.

The interior of the image reading apparatus 200 comprises a transfer section 220, a reading section 230, an erasing section 240, a control section 250. The transfer section 220 transfers the cassette 20 between the loading port 201A and the discharging port 201B. The reading section 230 reads the radiograph accumulated and recorded on the IP 10. The erasing section 240 erases the radiograph remaining on the IP 10. The control section 250 controls operations of the entire image reading apparatus 200, and transmits the radiograph read by the reading section 230 to the controller 300.

Once the sensor detects that the cassette 20 is attached to the image reading apparatus, a motor mounted on the lid member 210A of the loading port 201A is driven in accordance with the instruction from the control section 250. Thereby, the lid member 210A is opened. The cassette 20 loaded in the loading port 201A is transferred to the transfer section 220 by transfer rolls 2211.

The transfer section 220 is provided with two guide rails 222 and 223 as well as a transfer member 224. One of the two guide rails 222,223 is arranged above the other. Each of the two guide rails joins a loading position S1 under the loading port 201A, a reading position S2 under the reading section 230, an erasing position S3 under the erasing section 240, and a discharging position S4 under the discharging port 201B.

The transfer member 224 is configured to move along the guide rails 222 and 223, and to thereby transfer the cassette 20 between the loading position S1 and the discharging position S4.

First of all, the cassette 20 which has been transferred by the transfer rolls 2211 is held by the transfer member 224 at the loading position S1. Thereafter, the cassette 20 is transferred along the guide rails 222 and 223 to the reading position S2. A lid opening section 225 configured to open the lid 21 of the cassette 20 is arranged in a vicinity of the upper guide rail 222 at the reading position S2. A discharging section 226 is arranged in the lower guide rail 223. The discharging section 226 has two pins and a solenoid for inserting and pulling out the two pins. Once the cassette 20 is transferred to the reading position S2, the lid opening section 225 opens the lid 21 of the cassette 20, and thus the pins provided at the discharging section 226 are inserted in the push holes 20a and 20b. Hence, the IP 10 is pushed out of the cassette 20. The IP 10 which has been pushed out of the cassette 20 is transferred to the reading section 230 by transfer rolls 2212. The cassette 20 which is empty after the IP 10 is discharged from the cassette 20 is transferred along the guide rails 222 and 223 to the erasing position S3.

The reading section 230 is provided with a transfer route R which extends upward in the vertical direction. The reading section 230 includes shutters 231A and 231B, an excitation light irradiating section 233, an image reading section 235, two guide rails 236 and 237, and a pair of nip rolls 238 and 239. The shutters 231A and 231B are provided at two parts through which the IP 10 enters and exits. The excitation light irradiating section 233 irradiates an excitation light L in a main scanning direction (equal to a direction from the front to the back of the paper on which FIG. 3 is drawn). The image reading section 235 collects photostimulated luminescent light by use of a collective guide 234 extending in the main scanning direction, and to thus read the radiograph which has been accumulated and recorded on the IP 10. The guide rails 236 and 237 extend in the horizontal direction. One of the two guide rails is arranged above the other. The pair of nip rolls 238 and 239 are configured to transfer the IP 10 in the horizontal direction. One of the pair of nip rolls is arranged above the other of the pair of nip rolls. The upper nip roll 238 moves along the guide rail 236, and the lower nip roll 239 moves along the guide rail 237.

The IP 10 which has been discharged from the cassette 20 is transferred in the upward direction along the transfer route R toward the guide rails 236 and 237 by transfer rolls 2321 and 2322. Once the forward edge of the IP reaches the elevation at which the excitation light irradiating section 233 is arranged, the shutters 231A and 231B are closed. Thus, the interior of the reading section 230 is blocked from light. The IP 10 is transferred further upward by transfer roll 2322 and 2323. Subsequently, the excitation light irradiating section 233 irradiates excitation light L on the IP 10 which is being transferred. Thus, the image reading section 235 reads photostimulated luminescent light emitted from the IP 10. A radiograph which has been read by the image reading section 235 is transmitted to the control section 250, and thereafter is transmitted to the controller 300 as shown in FIG. 2.

In addition, the IP 10 from which the radiograph has been read is transferred to the nip rolls 238 and 239 by the transfer rolls 2322 and 2323. Thus, the IP 10 is nipped by the nip rolls 238 and 239. The nip rolls 238 and 239 move along the guide rails 236 and 237 in the horizontal direction while holding the IP 10. Once the nip rolls 238 and 239 reach the ends of the respective guide rails 236 and 237, the IP 10 is transferred downward. The IP is moved further downward by transfer rolls 2324 and 2231, and is transferred to the erasing section 240.

The erasing section 240 is provided with multiple fluorescent lamps 241 which are arranged both in the main scanning direction (equal to a direction from the front to the back of the paper on which FIG. 3 is drawn) and in a sub-scanning direction (equal to a direction from the top to the bottom of the paper on which FIG. 3 is drawn). Once erasing light Q is emitted from the multiple fluorescent lamps 241, the erasing light Q is irradiated on the IP 10 which is being transferred. As a result, the radioactive energy which has been accumulated on the IP 10 is discharged from the IP 10, and thus the radiograph is erased.

The IP 10 from which the radiograph has been erased is transferred further downward by the transfer rolls 2214. Thus, the IP 10 is housed in the cassette 20 which has been empty, and which has been transferred to the erasing position S3. A lid closing section 227 for closing the lid 21 of the cassette 20 is arranged at the erasing position S3. Once the IP 10 is housed in the cassette 20, the lid 21 of the cassette 20 is closed.

The cassette 20 housing the IP 10 from which the radiograph has been read, and from which the radioactive energy has been discharged, is transferred along the guide rails 222 and 223 to the discharging position S4.

A lid member 210B is arranged in the discharging port 201B as in the case of the loading port 201A. Once the cassette 20 is transferred to the discharging position S4, the lid member 210B of the discharging port 201B is opened. The cassette 20 which has been transferred to the discharging position S4 is transferred toward the discharging port 201B by transfer rolls 2215, and is discharged from the discharging port 201B.

In the foregoing manner, a radiograph is made, and the radiograph which is accumulated and recorded on the IP 10 is read.

In the the mammography apparatus 100 as shown in FIG. 2, the contact side surface 22 of the cassette 20 is pressed against the chest wall 2a of an object, and thus the mamma 2 is radiographed. If the cassette 20 is formed of a thicker plastic, the distance from the chest wall 2a to the IP 10 housed in the cassette 20 is accordingly longer. This makes it impossible to radiograph part of the mamma 2 closer to the chest wall 2a. On the other hand, if the cassette 20 is formed of a thinner plastic, a missing portion corresponding to the part of the mamma 2 which could not be otherwise radiographed is eliminated from the radiograph. However, this configuration brings about a problem that the strength of the cassette 20 decreases so that the cassette 20 is incapable of protecting the IP 10. The problem of this kind is solved in the IP 10 and the cassette 20 according to the present embodiment. Descriptions will be provided below for the configurations of each of the IP 10 and the cassette 20.

Figure 4:
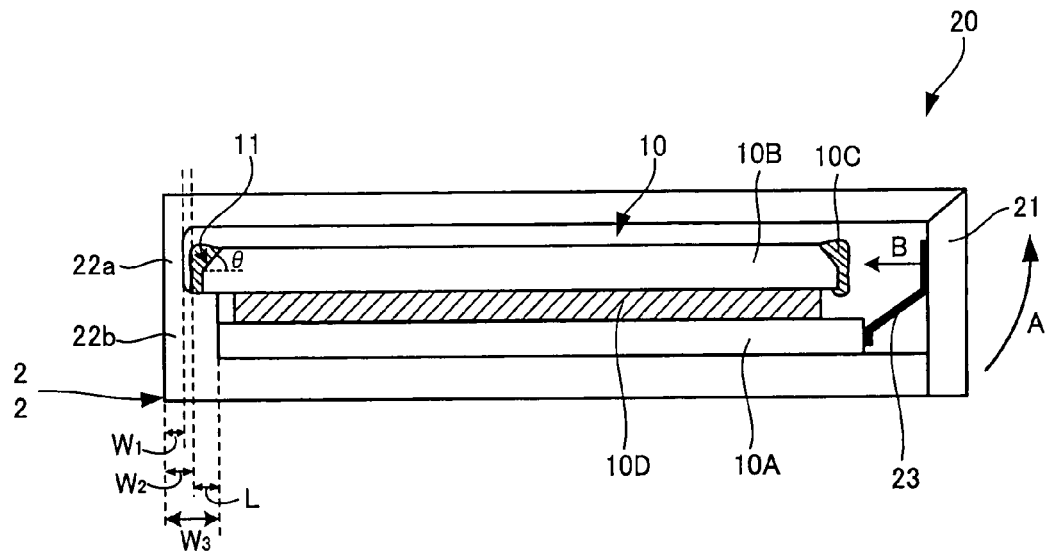
FIG. 4 is a cross-sectional view of the cassette which houses the IP, taken along A-A' line of FIG. 1.
Figure 5:
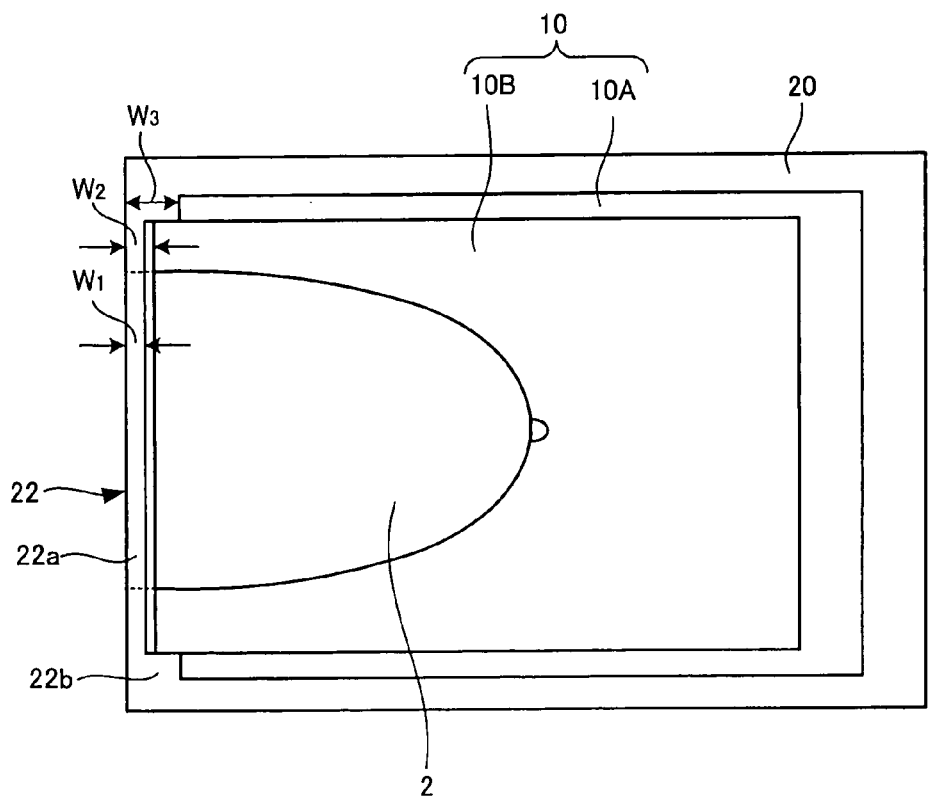
FIG. 5 is a conceptual diagram illustrating an image of a radiograph to be accumulated and recorded on the IP.

FIG. 4 is a cross-sectional view of the cassette housing the IP, which is taken along the A-A' line of FIG. 1. FIG. 5 is a conceptual diagram illustrating an image of a radiograph to be accumulated and recorded on the IP.

As shown in FIG. 4, the IP 10 is obtained by superposing the sheet 10B of the radioactive-energy-accumulating fluorescent substance on the substrate 10A with an adhesive 10D interposed in-between such that an end portion including an edge 11 of the sheet 10B of the radioactive-energy-accumulating fluorescent substance is shifted from the corresponding end portion of the substrate 10A, and by adhering the sheet 10B to the substrate 10A with the adhesive 10D. As a result, a step is formed in a side surface of the IP 10. The IP 10 is housed in the cassette 10 such that the side surface of the sheet 10B, in which the end portion of the sheet 10B of the radioactive-energy-accumulating fluorescent substance protrudes from the corresponding end portion of the substrate 10A, is opposed to the contact side surface 22 of the cassette 20. The end portion of the sheet 10B which protrudes from the corresponding end portion of the substrate 10A is an example of the front portion as recited in the present invention.

The both edges 11 of the sheet 10B of the radioactive-energy-accumulating fluorescent substance are chamfered at an elevation angle θ of approximately 70 degrees to 85 degrees to the horizontal plane. The chamfered edges 11 are each provided with a protection material 10C.

The cassette 20 is formed in such a way that the thickness W1 of a wall of a recording-side portion 22a is smaller than the thickness W3 of a wall of a substrate-side portion 22b in the contact side surface 22. The recording-side portion 22a in the contact side surface 22 is opposed to the sheet 10B of the radioactive-energy-accumulating fluorescent substance of the IP 10. The substrate-side portion 22b in the contact side surface 22 is opposed to the substrate 10A of the IP 10. It should be noted that the length L of the end portion of the sheet 10B of the radioactive-energy-accumulating fluorescent substance which protrudes from the corresponding end portion of the substrate 10A is smaller than the difference (W3−W1) between the thickness W3 of the wall of the substrate-side portion 22b and the thickness W1 of the wall of the recording-side portion 22a. Thereby, a slight space intervenes between the sheet 10B of the radioactive-energy-accumulating fluorescent substance and the recording-side portion 22a. In addition, the recording-side portion 22a of the cassette 20 is processed with an angle R. The lid 21 of the cassette 20 is provided with a plate spring 23 configured to bias the IP 10, which is housed in the cassette 20, toward the contact side surface 22. The recording-side portion 22a is an example of the opposed portion as recited in the present invention. The plate spring 23 is an example of the press member as recited in the present invention.

Once the IP 10 is housed in the cassette 20, the sheet 10B of the radioactive-energy-accumulating fluorescent substance is fitted into the recording-side portion 22a of the cassette 20. In addition, the substrate 10A is biased by the plate spring 23, and thus is pressed against the substrate-side portion of 22b of the cassette 20. Thereby, the sheet 10B of the radioactive-energy-accumulating fluorescent substance comes closer to the contact side surface 22 of the cassette 20. It should be noted that the edges 11 of the sheet 10B of the radioactive-energy-accumulating fluorescent substance are chamfered, and are each provided with the protection material 10C. In addition, the recording-side portion 22a of the cassette 20 is processed with the angle R. Moreover, the slight space intervenes between the sheet 10B of the radioactive-energy-accumulating fluorescent substance and the recoding-side portion 22a. These arrangements make it possible to reduce disadvantages including damage of the IP 10 which might otherwise occur when the sheet 10B of the radioactive-energy-accumulating fluorescent substance hits the cassette 20 while the IP 10 is being housed in the cassette 20.

Subsequently, the cassette 20 housing the IP 10 is attached to the mammography apparatus 100 as shown in FIG. 2, and the chest wall of the object is pressed against the contact side surface 22 of the cassette 20. Thereby, the sheet 10B of the radioactive-energy-accumulating fluorescent substance of the IP 10 comes closer to the base of the mamma 2 (the chest wall) of the object, as shown in FIG. 5. That is because the sheet 10B of the radioactive-energy-accumulating fluorescent substance of the IP 10 comes forward to the contact side surface 22 of the cassette 20 than the substrate 10A.

The conventional type IP and cassette have a disadvantage that, in a case where a radiograph is intended to be made after housing the IP in the cassette, the IP and the cassette are incapable of radiographing part of the mamma in a range of approximately several millimeters from the chest wall of an object. However, in the case of the IP 10 and the cassette 20 according to the present embodiment, the thickness W1 of the wall of the recording-side portion 22a of the cassette 20 is smaller compared with that of the conventional IP and cassette, and thus the sheet 10B of the radioactive-energy-accumulating fluorescent substance of the IP 10 comes closer to the contact side surface 22 of the cassette 20. This makes it possible to reduce a missing portion of the radiograph to a width in a range of approximately 0.5 mm from the chest wall. In addition, the thickness W3 of the wall of the substrate-side portion 22b opposed to the substrate 10, and which has nothing to do with the recording of the radiograph, is larger. This makes it possible to increase the strength of the cassette 20 without increasing the distance W2 between the sheet 10B of the radioactive-energy-accumulating fluorescent substance and the contact side surface 22 of the cassette 20.

As described above, the present invention makes it possible to reduce a missing portion of a radiograph to be made by a mammography apparatus without decreasing the strength of the cassette 20, and to thus detect a small tumor or the like in a position closer to the chest wall securely.

The descriptions for the first embodiment of the present invention end with the preceding paragraph. From now, descriptions will be provided for a second embodiment of the present invention. An IP and a cassette according to the second embodiment of the present invention have the substantially same configurations as the IP and the cassette according to the first embodiment of the present invention have. For this reason, in the second embodiment, elements which are the same as those of the first embodiment are denoted by the same reference numerals, and the descriptions for the elements will be omitted. The second embodiment will be described while focusing on what makes the second embodiment different from the first embodiment.

Figure 6:
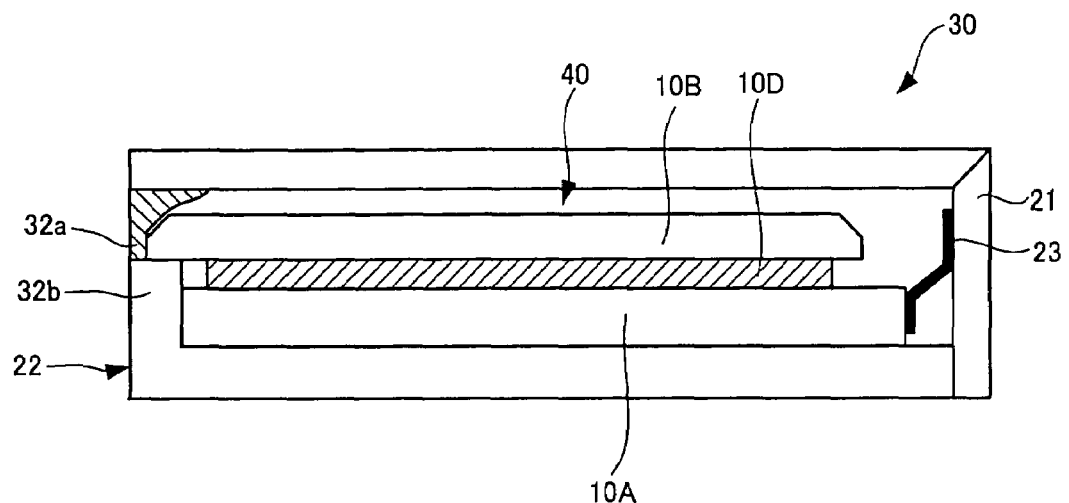
FIG. 6 is a cross-sectional view of an IP and a cassette according to a second embodiment of the present invention, taken along the A-A' line of FIG. 1.

FIG. 6 is a cross-sectional view of the IP and the cassette according to the second embodiment of the present invention, taken along the A-A' line of FIG. 1.

An IP 40 according to the present embodiment has the substantially same configuration as the IP 10 according to the first embodiment as shown in FIG. 4 has. The IP 40 according to the present embodiment is different from the IP 10 according to the first embodiment in that the IP 40 is not provided with the protection material 10C.

In addition, a cassette 30 according to the present embodiment has the substantially same configuration as the cassette 20 according to the first embodiment as shown in FIG. 4 has. The cassette 30 according to the present embodiment is different from the cassette 20 according to the first embodiment in that neither a recording-side portion 32a opposed to the sheet 10B of the radioactive-energy-accumulating fluorescent substance of the IP 40 nor a substrate-side portion 32b opposed to the substrate 10A of the IP 40 is processed with the angle R, and in that the recording-side portion 32a is configured of a material (for example, a sponge) which dents when pressed.

Once the IP 40 is inserted in the cassette 30, the substrate 10A is biased by the plate spring 23, and thus is pressed against the substrate-side portion 32b of the cassette 30. In addition, the sheet 10B of the radioactive-energy-accumulating fluorescent substance presses, and thus dents, the recording-side portion 32a. Thereby, the sheet 10B of the radioactive-energy-accumulating fluorescent substance comes closer to the contact side surface 22 of the cassette 30. Because the recording-side portion 32a is configured of a pliable material such as a sponge as described above, the IP 40 and the cassette 30 are capable of causing the sheet 10B of the radioactive-energy-accumulating fluorescent substance to come closer to the contact side surface 22 of the cassette 30 securely, and concurrently capable of preventing the sheet 10B of the radioactive-energy-accumulating fluorescent substance from being damaged, even if there is a dimensional error such as a too-long protruding portion of the sheet 10B of the radioactive-energy-accumulating fluorescent substance.

The descriptions for the second embodiment of the present invention end with the preceding paragraph. From now, descriptions will be provided for a third embodiment of the present invention. An IP and a cassette according to the third embodiment of the present invention have the substantially same configurations as the IP and the cassette according to the first embodiment of the present invention have. For this reason, in the third embodiment, elements which are the same as those of the first embodiment are denoted by the same reference numerals, and the descriptions for the elements will be omitted. The third embodiment will be described while focusing on what makes the third embodiment different from the first embodiment.

Figure 7:
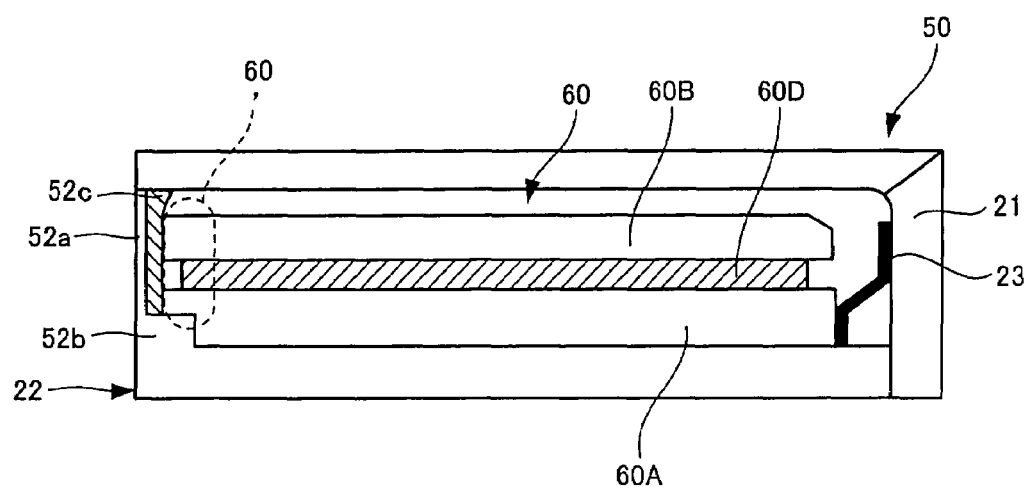
FIG. 7 is a cross-sectional view of an IP and a cassette according to a third embodiment of the present invention, taken along the A-A' line of FIG. 1.

FIG. 7 is a cross-sectional view of the IP and the cassette according to the third embodiment of the present invention, taken along the A-A' line of FIG. 1.

As described above, the IP 10 according to the first embodiment is obtained by adhering the sheet 10B of the radioactive-energy-accumulating fluorescent substance to the top of the substrate 10A in a way that the sheet 10B of the radioactive-energy-accumulating fluorescent substance is shifted, as shown in FIG. 4. Unlike the IP 10 according to the first embodiment, however, an IP 60 according to the present embodiment is obtained by forming a step in a side surface of a substrate 60A, adhering a sheet 60B of the radioactive-energy-accumulating fluorescent substance to the top of the substrate 60A, and thereby forming a protruding portion 60' which is configured of the sheet 60B of the radioactive-energy-accumulating fluorescent substance and the upper portion of the substrate 60A. The forming of the protruding portion 60' of the sheet 10B of the radioactive-energy-accumulating fluorescent substance and the upper portion of the substrate 60A makes it possible to increase the strength of the protruding portion 60'. This protruding portion 60' is also an example of the front portion as recited in the present invention.

In addition, in the case of a cassette 50 according to the present embodiment, a recording-side portion 52a opposed to the protruding portion 60' of the IP 60 dents under a substrate-side portion 52b opposed to a lower portion of the substrate 60A. The recording-side portion 52a is provided with a cushioning material 52c (for example, leather) configured to absorb a shock which occurs when the protruding portion 60' hits the recording-side portion 52a. The cushioning material 52c is an example of a shock absorbing member as recited in the present invention.

The IP 60 and the cassette 50 according to the present embodiment make it possible to efficiently suppress breaking of the sheet 60B of the radio-energy-accumulating fluorescent substance, because the strength of the protruding portion 60' of the IP 60 is increased, and because a shock on the protruding portion 60' is absorbed by the cushioning material 52c of the cassette 50.

The foregoing descriptions have been provided for the case where the two steps are formed in the side surface of the IP. In the case of the image recording plate as recited in the present invention, however, three steps or more may be formed in the side surface.

In addition, the foregoing descriptions have been provided for the case where the plate spring is used as the biasing member configured to bias the IP toward the cassette. In the case of the biasing member as recited in the present invention, however, any elastic member other than the plate spring may be used as the biasing means.

EXAMPLE

Descriptions will be provided below for an example of the present invention.

(1) Preparation of Various Members Constituting IP

A plane substrate (with the in-frame dimension of 174 mm×239 mm), a radiograph converting panel (with the dimension of 178 mm×238 mm; its edge is chamfered) and a double-sided adhesive sheet (with a dimension of 172 mm×237 mm, a 3M product, 4597FL) were prepared for use. A POM (polyoxymethylene)-made frame with a 0.7-mm height and a 5-mm width was formed in the two short sides and one long side of the plane substrate. Specifically, the radiograph converting panel was prepared by using the same method as in the example described in US Patent Publication Number 2006/0065852 A1.

(2) Adhesion of Double-Sided Adhesive Sheet to Substrate

First of all, a detachment film on the top side of the double-sided adhesive sheet was peeled off to expose the adhesive surface on the top side.

Subsequently, the substrate with the frames formed thereon was fixed to the top of a base whose surface surrounded by the frames was flat or slightly dented. Thereafter, the top of the resultant substrate was cleaned of dust. Afterward, the double-sided adhesive sheet was brought into intimate contact with the approximate center of the surface of the substrate surrounded by the frames. The double-sided adhesive sheet thus adhered was visually observed, and neither dust nor an air bubble was seen.

(3) Adhesion of Radiograph Conversion Panel to Substrate

The radiograph conversion panel was obtained by chamfering the edge portion of the layer of the fluorescent substance, and by thereafter applying resin to the edge. Subsequently, the radiograph conversion panel was adhered to the resultant substrate with the double-sided adhesive sheet interposed in-between such that the two marginal end portions of the radiograph conversion panel protrude from the long side of the substrate without a frame by 2 mm (the short sides of the substrate correspond to the short sides of the radiograph converting panel, respectively). Here, a portion of the radiograph conversion panel which protrudes from the substrate is equal to a protruding portion of the IP which will be described later. Incidentally, the remaining detachment film of the double-sided adhesive sheet on the substrate was peeled off immediately before adhering the radiograph conversion panel to the substrate. The radiograph conversion panel thus adhered was visually observed, and no damage was seen on the radiograph converting panel from the long side of the substrate which was provided with no frame.

(4) Preparation of Cassette and Insertion of IP in Cassette

A cassette as follows was prepared for use. The IP was capable of being inserted in the cassette from the long side thereof. The interior of the cassette had a 0.5-mm play in total. The side farthest away from the insertion port of the cassette had a concave portion capable of accommodating the protruding portion (2 mm) of the IP. More specifically, the concave portion is a groove with a 2.3-mm depth, a 1.0-mm width and a 240-mm length. Furthermore, the insertion lid was provided with a spring mechanism configured to bias the IP inward by 500 gf. When the IP was inserted in the cassette, a positional relationship between the side end of the layer of the fluorescent substance on the protruding portion of the IP which was the farthest away from the insertion port of the cassette and the external side end of the cassette which was the farthest away from the insertion port of the cassette represented a 0.5 mm difference in distance between the two.

(5) Radiographing for Mammography

The IP loaded in the cassette was radiographed by an X-ray generating apparatus with a Mo (molybdenum) tube (28 KV). In this occasion, a mammography phantom (a sample of an object) was placed on the radiographing surface of the cassette, and was arranged such that the external side of the cassette which was designed to contact the chest wall was brought into contact with one side of the mammography phantom. Subsequently, the mammography phantom was radiographed. Thereafter, the film was observed, and it was found that part of the radiograph of the mammography phantom was missing by 0.5 mm from the chest wall.

The present example made it possible to reduce a missing portion of the radiograph down to approximately 0.5 mm from the chest wall as described above, although, in the case of the conventional technique, part of a radiograph is missing by approximately 5 mm from the chest wall. By this, the present invention was proved to be effective.

It should be noted that, although the IP made of the radioactive-energy-accumulating fluorescent substance is used as the image recording plate, it goes without saying that the IP may be of an application type, of a vapor deposition type, or of any other type. The IP of the application type is obtained by dispersing the radioactive-energy-accumulating fluorescent substance in a binding agent, and by thus applying the resultant fluorescent substance. The IP of the vapor deposition type is obtained by forming the radioactive-energy-accumulating fluorescent substance in a column structure by vapor deposition.

In addition, a radiograph detector of a fixed-detector type may be used as the image recording plate. The radiograph detector of this type generates electric charges when irradiated with radioactive rays, and obtains a radiograph of an object by accumulating or reading the electric charges thus generated. In this case, unlike the IP, the radiograph detector used as the image recording plate need not be taken out of the cassette when the radiograph is going to be read from the image recording plate. However, the radiograph detector used as the image recording plate has the same effect as the IP used as the image recording plate has in a sense that a missing portion of a radiograph to be made can be reduced without decreasing the strength of the cassette.

What is claimed is:

1. An image recording carrier comprising:
    an image recording plate including a plate shaped supporter and a recording layer which is superposed on a top surface of the supporter, and which accumulates and records a radiograph when irradiated with radioactive rays carrying an image; and
    a cassette in which the image recording plate is housed,
    wherein the image recording plate has multiple steps formed in a direction along a thickness of the image recording plate on at least one side surface of the image recording plate, and has a front portion which is one of the multiple steps including the recording layer and which protrudes from the rest of the multiple steps, the cassette has a facing surface facing the side surface of the image recording plate while the image recording plate is housed in the cassette, and an opposed portion of the facing surface being opposed to the front portion of the image recording plate dents from the rest of the multiple steps.

2. The image recording carrier as recited in claim 1, wherein the front portion of the image recording plate is beveled.

3. The image recording carrier as recited in claim 1, wherein the opposed portion of the cassette is beveled.

4. The image recording carrier as recited in claim 1, wherein the cassette includes a press member which presses the image recording plate housed in the cassette toward the facing surface.

5. The image recording carrier as recited in claim 4, wherein the opposed portion of the cassette is configured of a material which changes in shape when a force is applied to the material so that the opposed portion dents when the press member presses the front portion against the opposed portion.

6. The image recording carrier as recited in claim 1, wherein an amount of dent of the opposed portion of the cassette is larger than an amount of protrusion of the front portion.

7. The image recording carrier as recited in claim 1, wherein the opposed portion of the cassette includes a shock absorbing member which absorbs a shock occurring when the front portion hits the opposed portion.

8. The image recording carrier as recited in claim 1, wherein an edge of the recording layer of the image recording plate is provided with a protection member which protects the edge.

9. The image recording carrier as recited in claim 1, wherein the image recording carrier is to be attached to a mammography apparatus.

* * * * *